United States Patent [19]

Hughes

[11] Patent Number: 5,063,912

[45] Date of Patent: Nov. 12, 1991

[54] SLEEP INDUCING DEVICE

[76] Inventor: John S. Hughes, 11 Bunyana Avenue, East Wahroonga, NSW 2076, Australia

[21] Appl. No.: 552,944

[22] Filed: Jul. 16, 1990

[51] Int. Cl.$^5$ .............................................. A61M 21/00
[52] U.S. Cl. ..................................... 128/33; 446/295; 600/28
[58] Field of Search ...................... 128/33, DIG. 15; 600/28, 27, 26; 446/295, 397, 297; 5/434, 436, 442

[56] References Cited

U.S. PATENT DOCUMENTS

| | | | |
|---|---|---|---|
| 2,512,641 | 6/1950 | Halstead | 5/434 |
| 2,958,769 | 11/1960 | Bounds | 5/442 |
| 4,124,022 | 11/1978 | Gross | 446/397 |
| 4,533,050 | 8/1985 | Bake, Jr. | 5/442 |
| 4,651,613 | 3/1987 | Harrison | 446/397 |
| 4,878,871 | 11/1989 | Noto | 446/297 |
| 4,941,453 | 7/1990 | Shakas et al. | 600/28 |

Primary Examiner—Edgar S. Burr
Assistant Examiner—Stephen R. Funk
Attorney, Agent, or Firm—McAulay Fisher Nissen Goldberg & Kiel

[57] ABSTRACT

A baby sleep inducer and calming method and device adapted for placement in a concealed or unobtrusive place in a baby crib or on a mattress, free of any connection to an energy source, having a housing for containing a self-contained source of energy and sound developer coupled thereto for producing a sound characteristic of a womb sound in the last four months of a foetus gestation period having a soothing, calming and sleep-inducing affect for a newborn infant when energized by the source of energy, which is free of external leads extending from the housing; the housing includes a protective casing to conceal and prevent unwanted access to the sound developer and the source of energy.

15 Claims, 5 Drawing Sheets

SLEEP INDUCING DEVICE

BACKGROUND OF THE INVENTION

This invention relates to a sleep inducer and baby calmer.

More particularly, the invention is concerned with a device which is portable and easily transportable by a parent or individual taking care of an infant, and who wants to take certain steps to induce a calming effect to a new born baby and in addition to calming the baby to induce a restful environment. For this purpose, it is desired to create or simulate an environment for the benefit of the baby as similar as possible to that just prior to the birth of the baby.

FIELD OF THE INVENTION

Infants, especially in the first few weeks after birth, may suffer stress from their worldly environment and detachment from their previous environment. This may result in the infant gaining less restfulness and less sleep than is desirable and this may cause long term effects in the personality of the child. Many parents have their own methods of soothing infants in order to calm them as well as to put them to sleep, and many devices have been proposed for this purpose. However, to date most proposals have not been widely accepted.

This invention aims to alleviate the above-mentioned disadvantages and to provide methods of and apparatus for the promotion of calmness sleep, particularly in infants.

DESCRIPTION OF THE PRIOR ART

Baby calmer and sleep inducing devices have been made heretofore. Among these are devices which attempt to simulate an intrauterine sound. A baby calmer disclosed in U.K. Patent Application No. 2,179,190A which provides for the production of a random noise of pseudo-random noise extending over an audio frequency range up to ten (10) kilohertz. The noise generated for a short period of time to attract the baby's attention and then it is switched to a lower level. This baby calmer does not use an intrauterine sound, but another sound of their own design. The noise or sound to be generated is first generated at a high level, then the sound is reduced to a lower level and, finally, the sound is cut-off or reduced to zero level. The higher level is to simulate a crying baby and the lower level is intended to lull the baby to sleep. The lower level noise is also intended to simulate the sound of a stream of water, wind through the trees, rain, etc., which are considered, according to the teachings of the published application, to be within a safe and pleasant limit. The basis of the disclosure is that a zener diode is an excellent source, according to the publication's teachings, of random noise, when used with a normal by-pass capacitor. Special timing circuits are also provided for the three different sound levels. The sound emitting device is housed within a shell.

Belkin, U.S. Pat. No. 3,292,611 is concerned with an infant mattress provided with heating and ticking mechanisms, primarily to distract or pacify an infant. The sounds emitted are intended to simulate a heart beat, and at the same time heat is generated. The device uses external leads and separate electrical energization which can be harmful to an infant both from the point of view of accidental strangulation as well as a fire hazard from the exposed wires, albeit covered wires.

U.S. Pat. No. 4,124,022 to Gross is concerned with a heart-shaped novelty and relaxation device which produces a slow heartbeat sound. The device employs an on-off switch, a speaker and circuitry for producing the slow heartbeat sound. The produced sound resembles the systolic and diastolic components of a human heartbeat at a pulse rate lower than the "normal" 72 beats per minute.

U.S. Pat. No. 4,157,088 to Gracey is concerned with a relaxation and massaging device in the form of a full body pad which is equipped with vibrating and heating devices to massage the body. A compact cassette tape player is disposed within the pad adjacent the portion to receive the head of the user.

U.S. Pat. No. 4,066,072 to Cummins is concerned with a fluid-filled flexible elastic sealed infant supporting mattress provided with a pulsating fluid pump. The purpose of the fluid pump is to simulate sounds of the human heartbeat upon opening and closing of the valves.

Chanery., U.S. Pat. No. 3,103,219 is concerned with a sleep inducing heating pad and is primarily intended for use with adults because the pad is so shaped to fit under the neck portion in the region between the overhang of the head and the upper portion of the back. Use is made of an external cable to supply electrical energy which can be detrimental to an infant. Foam rubber is shown for use as a cushioning material. However, there is no teaching or suggestion that this device is useable for calming or sleep inducement for a child.

U.S. Pat. No. 4,606,328 to Thoman discloses a surrogate type of mother or simulated animal which is provided with means to cause the body of the simulated animal to move so as to impart vestibular response as well as the simulation of breathing.

SUMMARY OF THE INVENTION

With the foregoing and other objects in view, this invention in one aspect resides broadly in a method of inducing calmness to a baby and to induce sleep to a baby, the method comprising: providing a resilient housing having a speaker assembly concealed therein; arranging the housing within a protective enclosure to prevent injury or stress to a baby for placement in proximity of or adjacent a mattress and playing soothing sounds through the speaker assembly to a baby resting on the mattress and providing a switching device for commencing the time period during which the sound to calm and induce sleep to the baby is to be emitted. The device is usable for infants and particularly new born infants, and for this purpose it is preferred that the sound recording be a recording of the natural womb sounds or intra-uterine sounds as heard by the baby before birth.

It is within the scope of the invention to substitute other sounds for calming and inducing the baby to sleep, and a portion of the unit is separately replaceable and interchangeable to provide different soothing sounds. Such other sounds, which may be used, may range for example, from a lullaby to repetitive noises or other noises or sounds which are known to or may be found to promote sleep.

Preferably, a combined unit composed of a sound developer, an amplifier and a speaker assembly are concealed within a pad-like protective covering which may be placed unobtrusively adjacent to the baby either beneath a mattress or the pillow used by the baby or a blanket, or it may be concealed within the baby bumpers which are placed around a crib to prevent the baby from injuring his or herself.

In another aspect, this invention resides broadly in a sound reproduction device which may be used for calming a baby for the sleep inducement method described above and including a resilient mounting for supporting an enclosure for a speaker assembly having associated therewith transmission means for transmitting a selected actuating, signal thereto. Preferably, the resilient mounting is a housing or outer casing which may be provided with a mounting cavity therein for receiving the speaker and sound producing assembly such that it may be completely concealed within the mounting pad which is an outer plastic foam covering or insulator.

It is also preferred that the speaker assembly not be connected to a remote player with an extension lead, and that no extension leads at all be used. Moreover, no structure is to be used which can have a deleterious effect on the baby. Preferably, a womb sound which is produced by a mother to be (a pregnant woman) is recorded on a tape and then reproduced electronically in a circuit to simulate the aforesaid womb sound.

Note, no wires or extension leads are used, and such leads do not have any deleterious effect on the baby. The housing or outer casing, preferably, is supported in a first casing or plastic covering which is then encased within a suitable foam rubber or other insulating material, such as an outer plastic foam covering. The foam protective material and first casing are then placed into a second casing which may be formed of fabric or a waterproof plastics material such as vinyl to provide a vinyl covering.

It is also preferred that the speaker concealed within the mounting pad be provided with a grill in the form of openings in the first casing to maintain the speaker opening of the mounting pad remote from the diaphragm of the speaker so that compression of the mounting pad will not adversely affect the performance of the speaker.

In a further aspect, this invention resides broadly in a method of forming a sound reproduction device, the method including providing a foam plastics pad into which the first casing is inserted; forming a slit substantially parallel to the major opposed faces of the pad to provide opposed flap portions; fitting the first casing together with the speaker assembly between the flap portions with no leads extending from the pad or first casing beyond the pad.

ADVANTAGES OF THE INVENTION

The sound pad in accordance with the present invention differs from existing sound pads in that all of the mechanisms are contained within the covering for the sound pad in the form of a mini cassette player with an in-built or built-in speaker system. No tape player is used as a microchip is used to simulate the womb sound. No external leads or wires are provided and the sound pad is totally portable. Power is provided from two 1.5 volts DC batteries.

While the sound pad is adapted to very young children, it can also be used for somewhat older children and adults of all ages, and the individual internal mechanism containing the sound chip can be packaged with various different sound chips to produce the desired sound or other desired musical or sound outputs.

ACHIEVEMENT OF WOMB SOUND

I have had a womb sound developed for me, which is characteristic of a natural womb sound, by inserting a microphone into a large number of wombs with an unborn infant within a pregnant woman to obtain the sound heard by an unborn child or fetus in the womb. An average of heartbeat, pulse rate, and other womb sounds from pre-birth mothers was achieved and transferred onto a cassette tape. It was then adjusted to achieve the best overall sound as a composite of the large number of womb sounds, together with the correct heartbeat and pulse rate. The composite womb sound is preferably derived from women who are at least five (5) months pregnant, to provide a newly born child and an infant with the sound atmosphere of a womb in the last five months of the gestation period. This is to produce as hospitable a condition as is possible for the young infant. After the average or composite of the various womb sounds was obtained, it was compared individually to each of the original womb sounds from which the composite was obtained, the composite womb sound was then transferred to a microchip.

BRIEF DESCRIPTION OF THE DRAWINGS

In order that the invention will be more readily understood and readily carried into effect, reference will now be made to the accompanying drawings which illustrate the preferred mode presently contemplated by me for carrying out the invention, in which.

DESCRIPTION OF THE PREFERRED EMBODIMENTS

Figure 1:
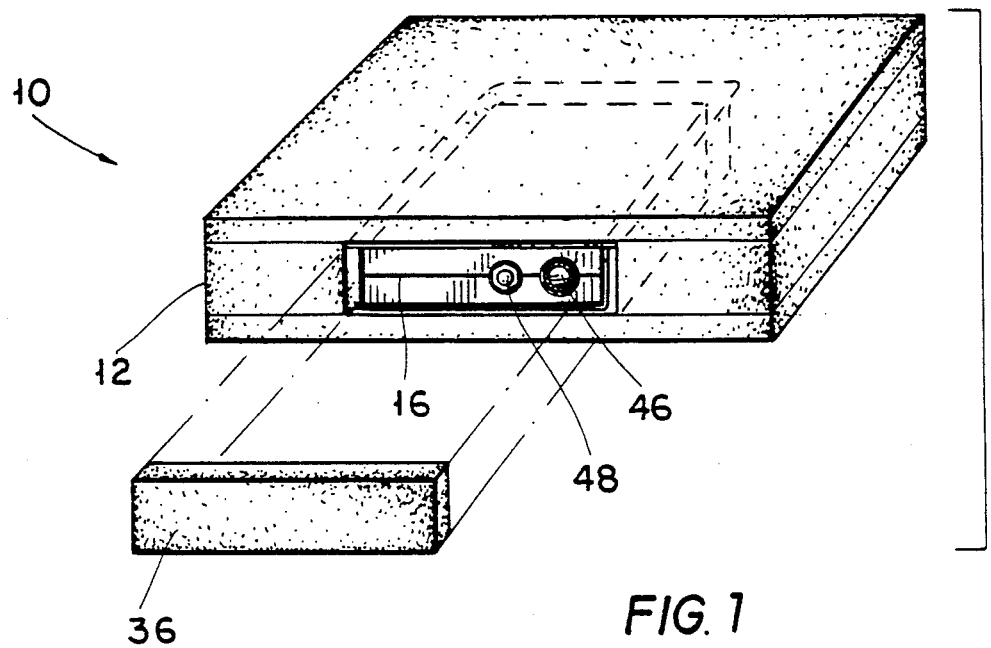
FIG. 1 is a perspective view of one embodiment of the baby calmer with an optional portion of the insulating material removed so that access to the controls is provided.

Referring now more particularly to the drawing, reference numeral 10 in FIG. 1 shows a baby calming and sleep inducing device which comprises an outer plastic foam insulator or protective covering or outer foam covering 12 which is positioned within a vinyl covering 14 (FIG. 4) to provide a soothing and pleasant and aesthetic appearance to the viewer. Contained within outer covering 14 is the foam enclosure for enclosing a self-contained sound reproducing mechanism 16. For protective purposes, sound reproducing mechanism 16 which is contained within housing or outer casing 40 may also be placed into a plastic covering 18 and then placed into foam enclosure or protective covering 12.

Figure 5:
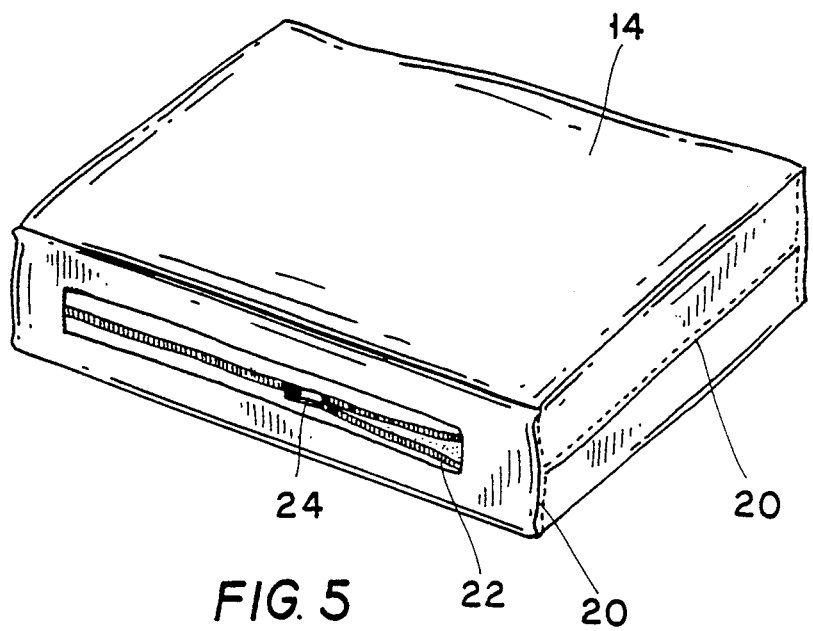
FIG. 5 is a perspective view of the baby calmer showing one modification of another covering.
Figure 6:
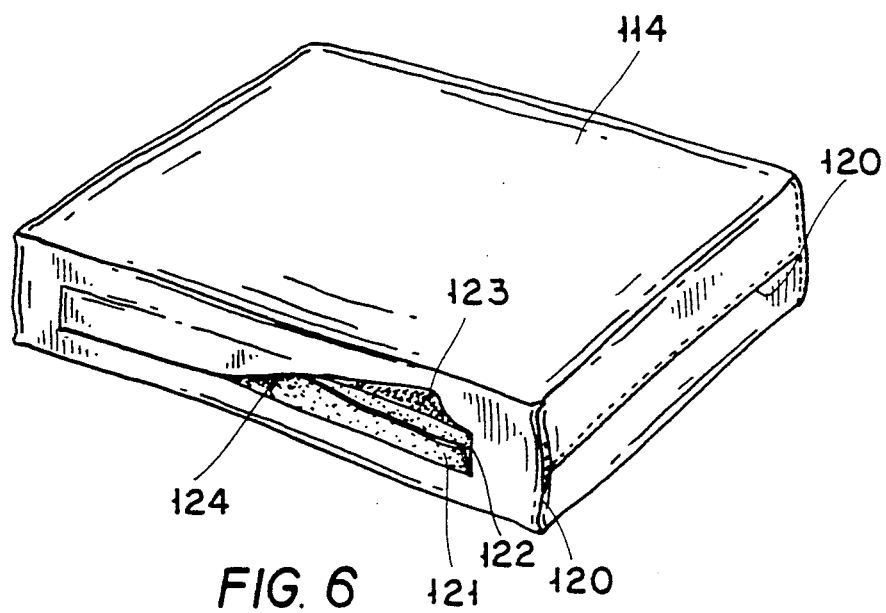
FIG. 6 is a modification of the baby calmer of FIG. 5 with a different closure for the outer covering.

Outer covering 14 is suitably made from a water-repellent vinyl material appropriately seamed by conventional heat sealing means at edge 20 to provide the necessary seals at the edges and an entry or opening portion 22 which is provided with a zipper closure mechanism 24 (FIG. 5) or other suitable closure (FIG. 6).

The protective casing means includes housing 40, protective covering 12 and outer covering 14. Outer covering 14 forms a casing which is softer than protective covering 12, and both are softer than housing 40.

Figure 2:
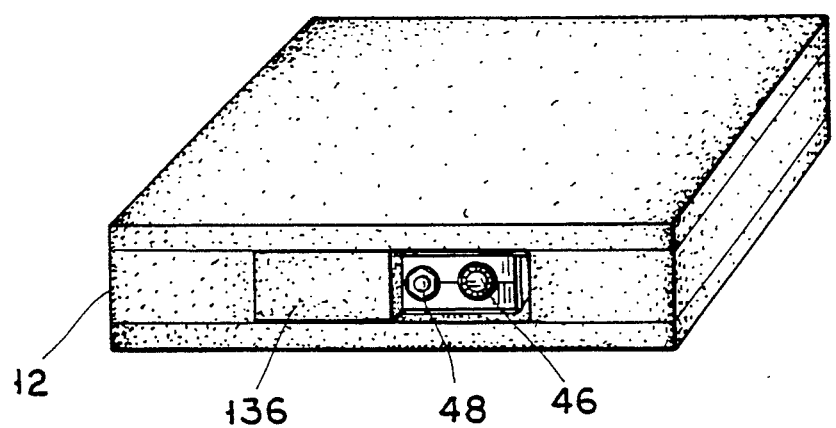
FIG. 2 is a view similar to FIG. 1, but showing another optional portion of the insulating material for closing off the access to the controls foreshortened and partially closing off the controls.
Figure 3:
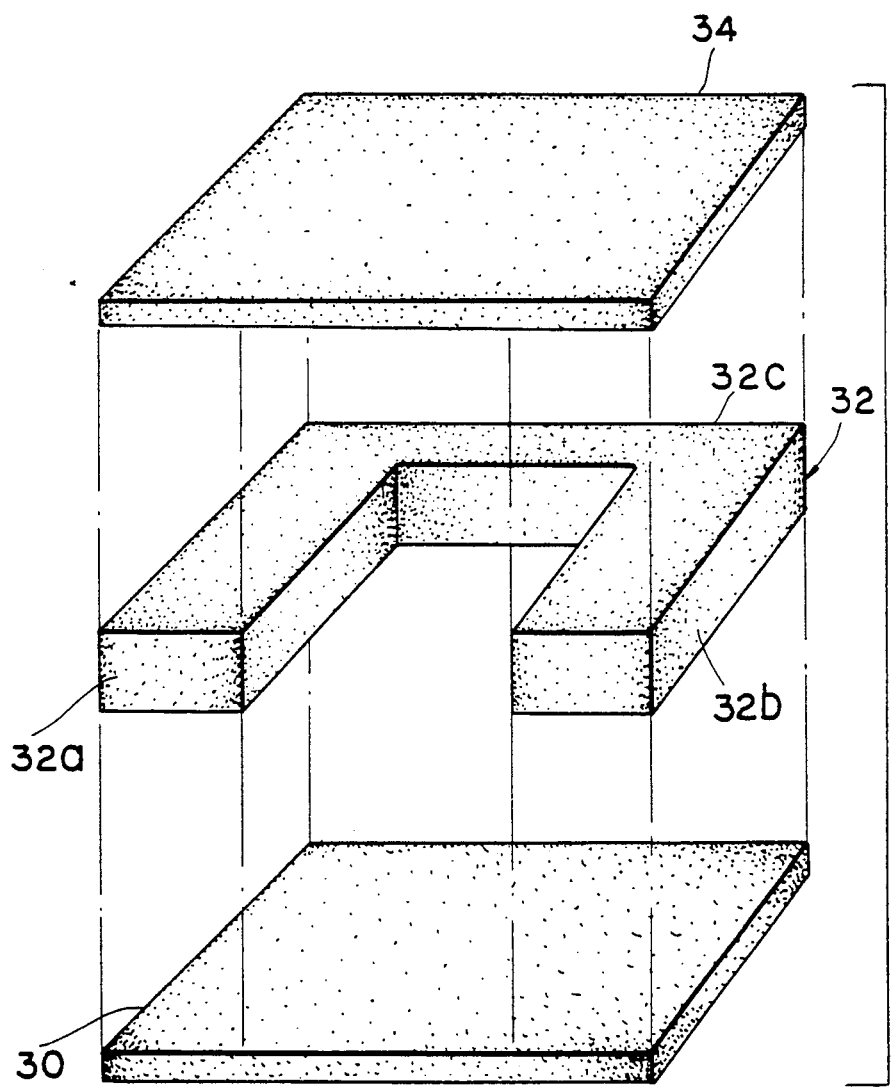
FIG. 3 is a modification of the outer insulating material portion.

Referring now to FIG. 3, foam enclosure 12 preferably includes a base portion 30, a U-shaped portion 32 which is adapted to rest on base portion 30 and a ceiling portion or roof portion 34 and a front closure 36 (FIG. 1) or partial front closure 136 (FIG. 2). Front closure portion 36 or partial front closure 136 is optional and may extend the entire extent between legs 32a and 32b and be parallel to base 32c of U-shaped portion 32 to receive front closure 36 or partial front closure 136. Front closure 36 Can be provided so that it fits between legs 32a and 32b so as to close off and seal opening 35 through which is inserted sound reproducing mechanism 16 and foam is provided on all sides to provide the same shielding all around sound reproducing mechanism 16. As will be explained later, access to the various controls can be provided by removal of the front closure 36. In addition, the foreshortened front closure 136, as shown in FIG. 2 may also be used so that the front closure portion 36 does not have to be removed in order to gain access to the controls.

Figure 4:
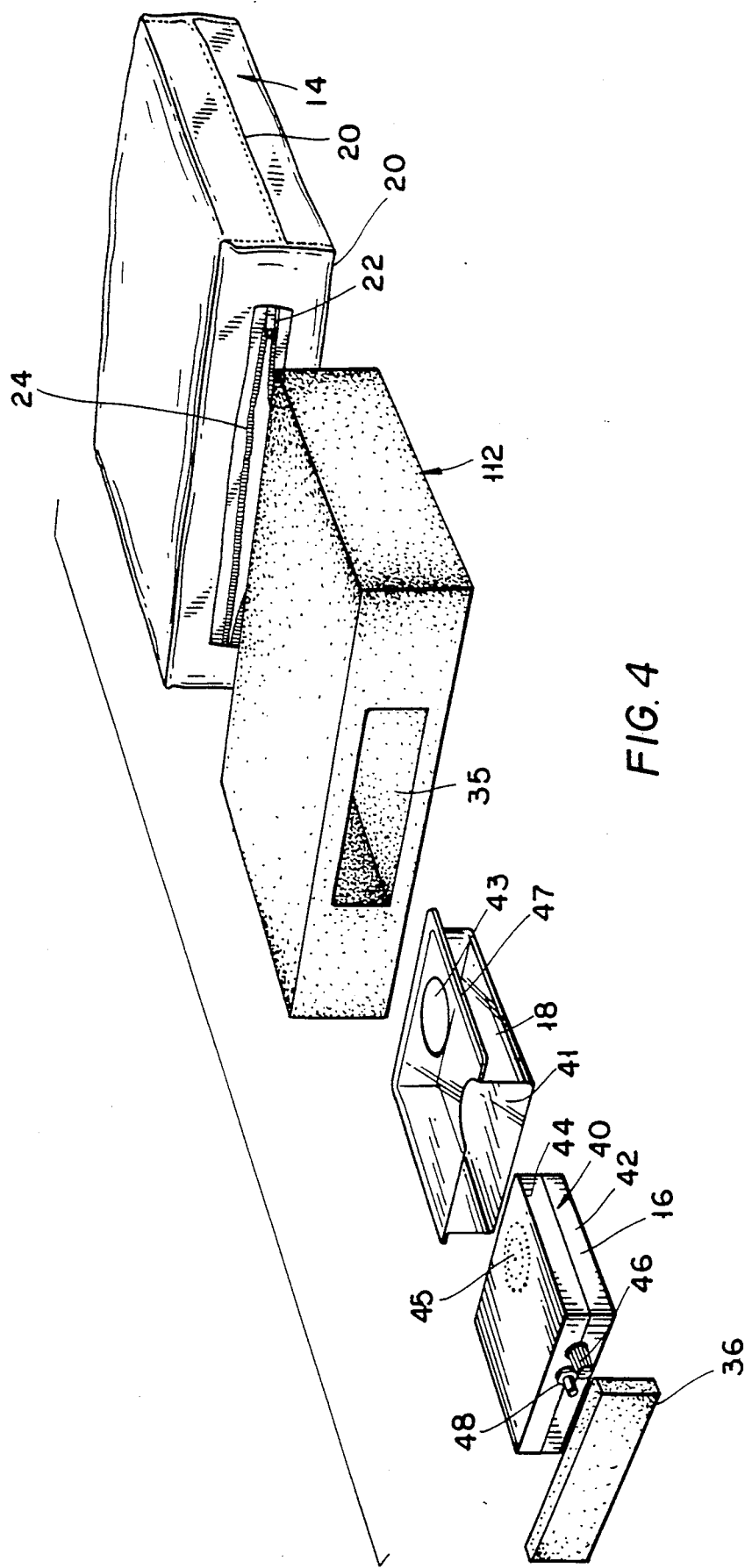
FIG. 4 is an exploded perspective view showing the various parts of the baby calmer and pacifier and employing a modification of the insulating material of FIG. 1.

Referring to FIG. 4 which shows an exploded view of another modification of outer foam covering 12 in FIG. 1 made as a single unit or single unitized foam covering 112 with an opening 35 forming a housing for sound reproducing mechanism 16 and optional plastic covering 18 of mechanism 16 is placed thereinto and used. Opening 35 is substantially rectangular on all sides to provide support to mechanism 16 or plastic covering 18 containing mechanism 16 and prevent it from shifting. It should be noted that either foam covering 12 or 112 can be used.

Optional plastic covering 18 is useful to provide a spacing between the openings or grill 45 to prevent the sounds from the internal speaker 49 from being squelched. This helps to maintain an adequate clearance between the speaker diaphragm and the enveloping foam plastics material. The housing 40 also assists for this purpose.

Sound reproducing mechanism 16 includes an outer hard plastic casing 40 comprising a base portion 42 and a top portion 44 provided with a speaker opening 45 to provide an opening for transmission of sound and, in this case, a womb sound. Knob 46 on the front face is an on-off knob and a volume control and knob 48 is a timer control to control the time period of the sound. The timer is set for a time period of twenty minutes. Housing 40 is made from a material much harder than the foam plastic covering 12 and optional plastic covering 18.

Plastic covering 18 is closed on all sides except that it is provided with a front opening 41 and another opening 43 which is a speaker opening in registry with opening 45 to provide for a transmission means for the sound outside of casing 40. Edge 47 is provided to facilitate assembly of plastic covering 18 and to facilitate insertion of covering 18 into opening 35. For this purpose, edge 47, when using the FIGS. 1 and 2 embodiments, glides between the top of U-shaped member 32 and fits between legs 32a, 32b, base 32c and roof portion 34. When the single unitized foam covering 112 is used, edge 47 can be used to fitably engage the plastic covering 18 with the internal volume generally indicated by reference numeral 35. Also, edge 47 may be sufficiently foreshortened to provide just sufficient room to seam weld the edges.

FIGS. 5 and 6 show two different outer coverings and closures. FIG. 5 shows the outer covering formed of vinyl 14 with a zipper closure 24 to cover insertion opening 22. Seam 20 may be seam welded to seal the different parts together to form the outer covering. FIG. 6 shows a cloth outer covering 114 with a stitched seam 120 and opening 122 closed by a VELCRO (a registered trademark) closure 124. VELCRO is registered trademark to indicate one type of closure which can be used for closure 124 includes a first member 121 which is closed by a second member 123 which overlies the first member 121, and members 121 and 123 form the closure 124 to provide simplicity in opening and closing opening 122 to facilitate removal of the plastic foam covering or insulator 12 for containing the sound reproducing mechanism 16.

Figure 7:
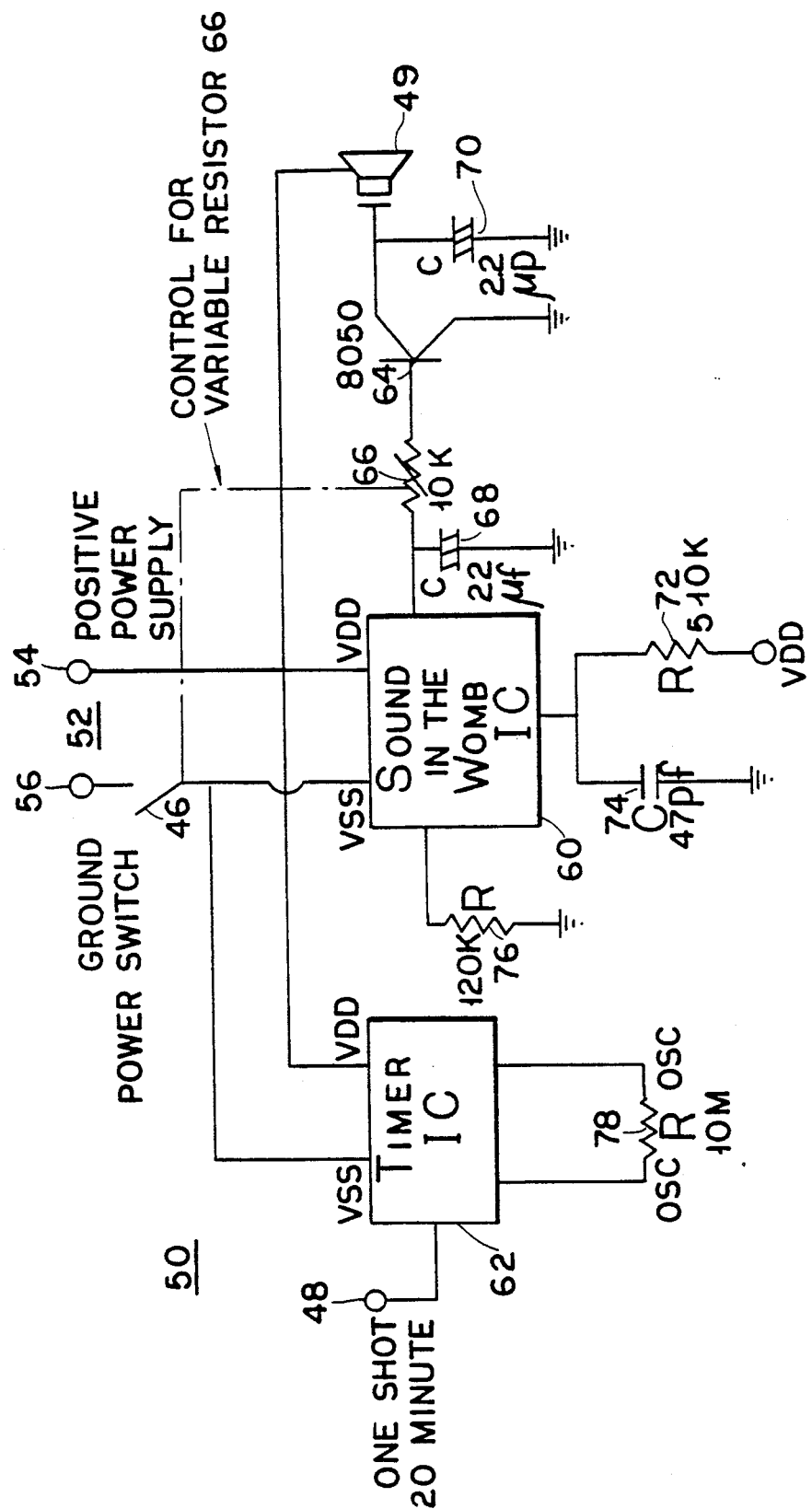
FIG. 7 is a circuit diagram showing the circuit for producing the womb sound.

Referring now more particularly to FIG. 7, which shows a preferred form of the circuitry to provide the composite womb sound, sound reproducing mechanism 16 which contains circuitry 50 including an output in the form of microphone speaker 49 all contained within enclosure or outer casing 40 which is provided with openings 45 for the sound from speaker 49 to go out from enclosure 40. On the outside of enclosure 40 is the push button switch or on-off and volume control knob, here schematically shown as switch 46 and the timer switch 48 connected with the circuitry schematically shown as a one shot 20 minute control. Variable resistor 66 (10K) is coupled to transistor amplifier 64 to control the volume of speaker 49 and volume control knob 46 to control the output of speaker 49. It is also possible to provide for a single push button switch and volume control and timer switch combination so that only a single one of the two buttons or controls are required for the on-off function, the volume control function and the timer function.

Circuitry 50 comprises an input from a positive power supply 52 having a conventional power supply terminals 54 and 56 which may be connected with two 1½volts DC batteries. The power supply includes positive terminal 54 and a negative or circuitry ground terminal 56 and timer switch 48. When power switch 46 is closed, the power switch is connected to a sound developer means in the form of a chip or integrated circuitry 60 capable of producing a womb sound derived from the womb sounds IC developed, as set forth heretofore, by inserting a microphone into a number of mother's-to-be or pregnant women's wombs. Also connected with power supply 52 is an internal timer 62 which provides for a timer circuit of preferably twenty minutes and activated in response to the push button actuator 48. The on-off switch 46 also performs the volume control function and is connected with volume control resistor 66.

The output of the womb sound chip 60 is applied to an amplifier circuit comprising a positive transistor 64 known as an 8050, which is fed from the chip circuit 60 through variable output resistor 66 (10 kilo-ohms) and isolated from the ground by capacitor 68 (22 μf). Variable resistor 66 is connected with the volume control portion of on-off control switch/knob 46 to control the volume output of the womb sound. The output from amplifier 64 is applied to speaker 49 and is isolated from ground by means of resistor 70. The womb sound device 60 is connected to volume control 46. Resistor 72 and capacitor 74 form a time constant circuit. Capacitor 74 (47 pf)is charged by womb sound chip and discharges through resistors 72 (510 kilo-ohms). VDD is a positive terminal and VSS is a negative or ground terminal, and resistor 72, capacitor 74 combination is connected across womb sound input-energizer. Resistor 76 (120 kilo-ohms) is a stabilizing resistor to prevent malfunctioning of womb sound means 60.

Timer circuit 62 is a multivibrator which includes an oscillator 78 which is pre-timed in the factory preferable for twenty minutes. While it may be timed for less than twenty minutes or more, I have found that twenty minutes is a preferred time period. Timer circuit 62 is connected with timer switch knob 48.

The RC circuit comprises resistor 72 (R510K) and capacitor 74 (C47Pf) and resistor 77 is a cycle frequency resistor. Womb sound integrated circuit 60 (IC) 510K is connected in circuit with VDD, 47Pf and with VSS to form a complete circuit. The RC circuit 72-74 is not connected with the timer, and it works independently of the circuit for the womb sound IC.

The womb sound chip is available from Peak Enterprises Corp. of 7FL., No. 187, Sec. 4, Hsin Yi Road, Taipei, Taiwan under the agreement by Joy Far Company Ltd.

While outer covering 14 is preferably made from a water-repellent vinyl material, other suitable outer covering materials may be used which will not impart any deleterious effect to a baby or adult user and be suitable for its intended purpose. While two separate knobs 46 and 48 are shown to control the on-off volume control and time period, it is within the scope of the invention to use a single knob for all three controls. Casing 40 may be as single unitized member and encased in molded plastic to prevent entry or access to the inner portion.

It will be evident that, while the unit is substantially self-contained and well insulated to prevent injury to an infant, it can be placed in various locations relative to an infant, so that the infant can hear the womb sound. The unit can be advantageously placed under a mattress or on the mattress and proximate to or juxtaposed to baby crib bumpers or other devices used to protect a baby or infant and insulate a baby/infant from any damage as a result of a foreign object being next to the baby/infant.

While there is shown what is presently considered to be the preferred embodiments, it will be obvious to those skilled in the art that various changes and modifications may be made therein without departing from the scope of the invention.

I claim:

1. A baby sleep inducer and calming device free of any connection to an energy source, comprising:
    a self-contained source of energy;
    housing means for preventing injury to a baby and containing said self-contained source of energy and sound developer means coupled thereto for producing a sound having the characteristic of a sound heard by a baby in a womb during the last four months of pregnancy and having a soothing, calming and sleep-inducing effect on a newborn infant when energized by said source of energy, said source of energy being free of external leads extending from said housing;
    said housing means including protective casing means to conceal and prevent unwanted access to said sound developer means and said source of energy;
    said protective casing means including:
    a first casing for said sound developer means and an internal speaker comprising a housing formed of a hard plastic material for enclosing said self-contained source of energy, said sound developer means, said speaker and all circuitry associated with said self-contained source of energy, said sound developer means and said speaker, said housing formed of said hard plastic material having control means externally thereof for controlling the sound duration and volume of the sound emitted from said sound developer means;
    a foam protective material somewhat softer than said first casing encompassing said housing formed of said hard plastic material for preventing injury to an infant when contacting said device, said foam plastic material having an access portion to provide access to said control means; and
    a second casing formed of a material softer than said first casing and said foam plastic material, including an outer covering formed of a waterproof plastic material and having an opening for access thereinto for insertion of said first casing formed of said hard plastic material and said foam protective material encompassing said hard plastic material of said first casing, and means for closing of said opening to prevent unwanted access thereinto and to prevent contamination of the interior of said first casing.

2. The device as claimed in claim 1, including a plastic covering positioned between said first and said second casings and covering said first casing.

3. A baby sleep inducer and calming device adapted for placement in a concealed place, free of any connection to an energy source, comprising:
    a self-contained source of energy;
    housing means for containing said self-contained source of energy and sound developer means coupled thereto for producing a sound having a soothing, calming and sleep-inducing effect on a newborn infant when energized by said source of energy, said source of energy being free of external leads extending from said housing;
    said housing means including protective casing means to conceal and prevent unwanted access to said sound developer means and said source of energy;
    said protective casing means including:
    a hard plastic housing for enclosing said self-contained source of energy, said sound developer means and all circuitry associated with said self-contained source of energy and said sound developer means, said hard plastic housing having control means externally thereof for controlling said sound developer means;
    a foam protective material encompassing said hard plastic housing and having an access portion to provide access to said control means, said foam protective material including a closer for closing off at least a part of said access portion formed of foam protective material to substantially enclose said hard plastic housing; and
    an outer casing formed of a water proof plastic material and opening thereinto for insertion of said hard plastic material and said foam protective material encompassing said hard plastic material, and means for closing of said opening to prevent unwanted access thereinto and to said control means and to prevent contamination of the interior of said outer casing.

4. The device of claim 3, wherein said closer closes off said access portion to form a complete enclosure free of an a opening or access to said hard plastic housing.

5. The device of claim 3, wherein said foam protective material includes a base foam plastic member on which said hard plastic housing rests, a U-shaped foam plastic member resting on said base member and encompassing three sides of said hard plastic housing leaving said access portion between a pair of legs of said U-shaped member, and a ceiling plastic foam member overlying said U-shaped member and said hard plastic housing.

6. The device of claim 5, wherein said closer fits within said access portion for closing off thereof and preventing access to said control means, said closer fitting between the legs of said U-shaped portion and between said base member and said ceiling member and on a side of said hard plastic housing said external control means.

7. The device of claim 4, including:
 a circuit for producing a natural womb sound as heard by a baby before birth comprising a womb sound chip means prepared from tapes derived from the womb sound of women who are pregnant and during the last four months of their pregnancy;
 speaker means coupled to said womb sound chip means through amplifier means for amplifying and producing an audible sound through said speaker means; and
 timer circuit means including a multivibrator and an oscillator coupled with said chip means for producing a periodic control of the output of said chip means.

8. The device of claim 4, wherein said closing means includes a zipper to close off said opening.

9. The device of claim 4, wherein said closing means includes VELCRO to close off said opening.

10. The device of claim 4, wherein said hard plastic housing includes a grill to provide openings for the sound to exit from said housing.

11. The device of claim 5, wherein said hard plastic housing has a grill to provide openings for said sound to exit from said housing.

12. The device of claim 5, wherein said closing means includes a zipper to close off said opening.

13. The device of claim 11, wherein said closing means includes VELCRO to close off said opening.

14. A method of forming a sound reproduction device for inducing a baby to sleep, including:
 providing a resilient housing having a speaker assembly concealed therein;
 providing a foam plastics pad;
 providing an outer protective covering for said foam plastics pad;
 forming a slit substantially parallel to major opposed faces of the pad to provide opposed flap portions;
 fitting the speaker assembly between said flap portion with any internal connections being contained within the pad;
 securing the flap portions; and
 providing start-stop means and timer means to start a sound characteristic of a womb sound heard by a baby during the last four months of the gestation period of a foetus and to control the duration of the sound.

15. The method of claim 14, including providing said foam plastics pad to completely enclose said resilient housing.

* * * * *